US005745548A

United States Patent [19]

Dobbs et al.

[11] Patent Number: 5,745,548

[45] Date of Patent: Apr. 28, 1998

[54] APPARATUS FOR AND METHOD OF ADJUSTABLY PRECALIBRATING THE POSITION OF THE FOCAL SPOT OF AN X-RAY TUBE FOR USE IN A CT SCANNER SYSTEM

[75] Inventors: John Dobbs, Hamilton; Ruvin Deych, Brookline; David Banks, Framingham, all of Mass.

[73] Assignee: Analogic Corporation, Peabody, Mass.

[21] Appl. No.: 800,587

[22] Filed: Feb. 18, 1997

Related U.S. Application Data

[63] Continuation of Ser. No. 563,658, Nov. 28, 1995, abandoned.

[51] Int. Cl.[6] .............................. G01D 18/00; A61B 6/08

[52] U.S. Cl. ........................... 378/207; 378/205; 378/206

[58] Field of Search .................................... 378/205, 206, 378/207; 250/252.1; 356/121, 122, 123

[56] References Cited

U.S. PATENT DOCUMENTS

| | | | |
|---|---|---|---|
| 2,880,557 | 4/1959 | Todd et al. | 356/121 |
| 4,139,776 | 2/1979 | Hellstrom | 378/25 |
| 4,356,400 | 10/1982 | Polizzi et al. | 378/138 |
| 4,991,189 | 2/1991 | Boomgaarden et al. | 378/4 |
| 5,257,051 | 10/1993 | Bushroe | 353/112 |
| 5,315,763 | 5/1994 | Wing | 33/288 |
| 5,469,429 | 11/1995 | Yamazaki et al. | 378/19 |
| 5,481,586 | 1/1996 | Coe | 378/146 |
| 5,550,886 | 8/1996 | Dobbs et al. | 378/19 |

FOREIGN PATENT DOCUMENTS

| | | |
|---|---|---|
| 0 165 850 | 12/1985 | European Pat. Off. . |
| 37 09 109 | 12/1988 | Germany . |
| 195 15 778 | 11/1995 | Germany . |

*Primary Examiner*—David P. Porta
*Assistant Examiner*—David Vernon Bruce
*Attorney, Agent, or Firm*—Lappin & Kusmer LLP

[57] ABSTRACT

The invention provides a system for and method of precalibrating the position of the focal spot of an X-ray tube before its installation in a CT scanner system so that the focal spot of the tube is properly aligned with the off-focal aperture, slice-defining aperture and detectors of the scanner system. The precalibration is performed using an interface registration support that receives the X-ray tube and supports the X-ray tube on a mount provided in either the precalibration system or the scanner system. The mount of the precalibration system duplicates the mount of the scanner system, so that desired position of the focal spot in the scanner system relative to the scanner system mount is duplicated in the precalibration system relative to the precalibration system mount. Adjustments in the position of the focal spot are carried out by measuring any displacement of the focal spot of the X-ray tube relative to an interface registration support which is referenced to the desired position of the focal spot by registering the registration support to the mount of the precalibration system. The as-adjusted X-ray tube and its interface registration support can then be installed in the CT scanner without the need for subsequent calibration adjustments. Additional testing of the X-ray tube can also be provided.

31 Claims, 6 Drawing Sheets

APPARATUS FOR AND METHOD OF ADJUSTABLY PRECALIBRATING THE POSITION OF THE FOCAL SPOT OF AN X-RAY TUBE FOR USE IN A CT SCANNER SYSTEM

This is a continuation of application Ser. No. 08/563,658 filed on Nov. 28, 1995 now abandoned.

FIELD OF THE INVENTION

This invention relates generally to calibrating the desired position of X-ray sources in X-ray systems, and more particularly to an apparatus for and method of adjustably precalibrating the focal spot of an X-ray tube relative to a detector array of a computed tomographic (CT) scanner system, prior to mounting the tube in the scanner system.

BACKGROUND OF THE INVENTION

A typical CT scanner system includes a gantry comprising an annular frame for rotatably supporting an annular disk about a rotation axis (hereinafter referred to as the "Z axis"). The disk includes a central opening large enough to receive a patient upon whom a scan is performed. In third generation type scanner systems an X-ray tube is positioned on one side of the disk diametrically across the central opening from a detector assembly comprising an array of detectors for counting X-ray photons. As the disk rotates the X-ray beam emanating from the X-ray tube and directed toward the detector array rotates in a common plane, hereinafter the "scanning plane", which hereinafter defines the X and Y axes mutually orthogonal to one another and to the Z axis. The X-rays directed toward the detector array emanate from a point in the X-ray tube usually referred to as the "focal spot". A pair of apertures are typically used in connection with and in part defining the radiation beam. One, referred to hereinafter as the "off-focal aperture" is for limiting the amount of radiation leaving the X-ray tube housing within which the tube is mounted. The other is referred to hereinafter as the "slice-defining aperture", and helps define the shape of the beam of radiation so that the beam is only directed toward the detector array. As shown in FIGS. 1 and 2, a precollimator, for defining the off-focal aperture, is typically positioned as close as is possible to the focal spot, while a collimator, for defining the slice-defining aperture, is typically placed as close to the patient as is practical. The detectors of the detector array are positioned so as to define a corresponding plurality of X-ray paths from the focal spot through the off-focal aperture and slice-defining aperture to the respective detectors within a common plane of rotation of the disk, i.e., the scanning plane. In third generation machines, the ray paths between the focal spot and the detectors resembles a fan, and hence the term "fan beam" is sometimes used to refer to the shape of the beam. The slice-defining aperture defines the thickness of the beam (in the Z axis direction) and limits the amount of radiation (passing from the focal spot through the off-focal aperture) to which the patient is exposed and directs this radiation beam toward the detectors.

The disk is normally adapted to rotate through at least a full 360 degree rotation about the Z axis so that the source rotates through a plurality of incremental positions where a corresponding series or set of readings (called "projections" or "views") by the detectors are made. The number of photons absorbed along the various ray paths through the patient, during each sampling period defining each projection, is a function of the absorption characteristics of the portions of the patient along each path during each set of readings. Thus, a plurality of projections are taken through the portion of a patient disposed within the common plane of rotation of the X-ray paths. The detectors generate a corresponding plurality of analog information signals representative of X-ray flux detected by the detectors during each sampling period or projection. These signals are processed by a data acquisition system (DAS).

The output analog information signals of the X-ray detectors acquired from all of the projections of the 360 degree rotation, i.e., through all of the incremental angular positions of the 360 degree rotation within the plane of rotation, are processed, typically through a convolution and back projection processing technique, so as to create a reconstructed image of the interior structure of the object exposed to the X-rays, typically in the form of a two-dimension image of a thin slice, the thickness being determined, as mentioned above, by the thickness of the slice-defining aperture.

In many machines as much as 15% of the X-rays coming from the X-ray tube housing may originate at points within the housing which are not within the focal spot of the X-ray tube. This off-focal radiation will cause problems with image quality if detected by any of the detectors of the detector array during the scan. While two apertures have been described, it is critical that in a given direction (within the scanning plane or in the Z axis direction) only one defines the aperture of the primary beam during the entire operation of the machine. If two elements are used to define the beam, relative motion between these elements will cause modulation of the beam intensity. This modulation will produce image artifacts, increased noise and drift in the calibration of the machine. For this reason the off-focal aperture must be large enough that it never affects the primary beam even with relative motion between the two apertures due, for example, to machine vibration. The beam defined by the focal spot and the off-focal aperture must fully illuminate the entire slice-defining aperture under all operating conditions.

Thus, the standard CT scanner system, based upon well established mathematical relationships, assumes that the components of the system, especially the source, off-focal aperture, slice-defining aperture and the detectors, are perfectly aligned relative to one another. In a typical third generation CT scanner system, when properly positioned, the focal spot is spaced at a distance on the order of about 125 mm to about 300 mm from the collimator and about 800 mm to about 1100 from each of the detectors of the detector array, so that the focal spot must be positioned ±0.1 mm of its precise (optimal) position in three dimensions, both within the scanning plane and in the Z axis direction. For example, in one scanner system the collimator is approximately 150 mm from the focal spot and the primary detector array is approximately 845 mm from the focal spot. In such a system, a 0.3 mm misalignment of the focal spot will result in a 1.7 mm misalignment of the beam on the detector array.

Thus, the accurate generation of imaging data requires that the focal spot of the X-ray tube be suitably aligned with the off-focal aperture, the slice-defining aperture and the detectors of the detector array when installing the tube on the disk of the scanner system. Any misalignment among these devices will adversely affect the ability of the imaging equipment to generate data that is accurately representative of the internal profile of the patient.

Prior to the present invention, the tube typically has been mounted on the CT scanner system and the position of the tube continuously adjusted until the correct position is empirically determined. This calibration process usually requires the installer to mount the tube as precisely as possible and then run the machine and measure the output of the detectors with the DAS to determine if the outputs are optimum, or if adjustments are required. The process of calibrating the position of the X-ray tube on the CT scanner system is time consuming and typically can take as much as two to four hours to complete. This is particularly troublesome when replacing the tube on existing CT scanner systems being used in the field, since the time required to replace the tube represents down time of the machine. A need therefore exists to properly configure a CT scanner system such that the X-ray source can be predictably aligned with the off-focal aperture, slice-defining aperture and detectors when the X-ray source is installed in the CT scanner system, without the need for further calibration, substantially reducing the time of installing a new tube than that currently required.

OBJECTS OF THE INVENTION

It is a general object of the present invention to provide an apparatus for and a method of precalibrating the position of an X-ray source for use in an X-ray system prior to mounting the source in the system so that when the source is mounted in the system no additional calibration is required.

It is a more specific object of the present invention to provide an apparatus for and a method of precalibrating the position of the focal spot of an X-ray tube relative to an off-focal aperture, slice-defining aperture and detector array of a CT scanner system prior to mounting the tube in the system so as to significantly reduce or overcome the problems of the prior art.

Another more specific object of the present invention is to provide apparatus for and a method of adjustably precalibrating the focal spot of an X-ray tube relative to a detector array of a computed tomographic (CT) scanner system, prior to mounting the tube in the scanner system.

And another object of the present invention is to provide a calibration testing system for and method of adjustably positioning the focal spot of an X-ray tube and fixably retaining the focal spot adjustment by integrating the as-adjusted X-ray tube with an interface registration support used to mount and register the X-ray tube in its proper position on a CT scanner system so that the focal spot will be precisely positioned relative to the off-focal aperture, slice-defining aperture and the detector array.

Yet another object of the invention is to provide a mounting structure for the integrated as-adjusted X-ray tube and interface registration support in order to facilitate the installation of the X-ray tube into a CT scanner.

Still another object of the present invention is to provide an improved apparatus for and method of adjustably precalibrating the focal spot of an X-ray tube for use in a CT scanner system and for installing the precalibrated tube in a CT scanner system in substantially less time than the prior art method of mounting the tube and calibrating the position of the focal spot on the scanner system.

And yet another object of the present invention is to reduce the size of the off-focal aperture of the precollimator so as to reduce the amount of stray radiation exiting the X-ray tube housing.

And still another object of the present invention is to provide a testing instrument for testing important operational parameters of the X-ray source.

SUMMARY OF THE INVENTION

In accordance with one aspect of the present invention, a calibration instrument is used to adjustably precalibrate the proper location of a radiation source adapted for use in a larger system prior to mounting the source in the system so that subsequent calibration of the location of the source once mounted on the system is not required. In the preferred embodiment, the calibration instrument allows an X-ray tube to be fixed in the calibrated location relative to an interface registration support. The X-ray system is provided with mounting means for receiving the interface registration support so that the X-ray tube will be precisely positioned in the calibrated location of the X-ray system without the need for additional calibration. The instrument is also capable of testing other important operational parameters of the X-ray tube.

In the preferred embodiment, the calibration instrument includes means for defining at least three beam paths which intersect at a predetermined point in space, which is, as will evident hereinafter, the desired spatial calibrated position for the focal spot of the X-ray tube when the tube is mounted in a CT scanner system. At least one detector is positioned in and defines each beam path. The detectors should be arranged so that when the focal spot of the X-ray tube being calibrated is located near the intersection point of the three beam paths, the direction and approximate magnitude of the displacement needed to place the focal spot of the source at the desired position can be determined.

The preferred calibration instrument also includes reference mounting means, preferably substantially identical to the mounting means of the CT scanner system, for receiving an X-ray tube assembly. The latter assembly includes the X-ray tube and an interface registration support so that when the tube assembly is mounted on the reference mounting means of the calibration instrument with the focal spot in the desired calibrated spatial position and fixed within the X-ray tube assembly relative to the interface registration support, the resulting tube assembly can be mounted on the corresponding mounting means of the CT scanner system for receiving the tube assembly, with the focal spot being correctly positioned relative to the off-focal aperture, slice-defining aperture and the detector array of the CT scanner system without the need for additional calibration.

The preferred tube assembly includes:

(a) the interface registration support comprising a mounting flange adapted to be secured to the mounting means of the instrument or the scanner system, with registration means being provided between the two parts to insure reproducible positioning of the mounting flange;

(b) a tube flange adapted to be fixedly secured to the X-ray tube and including registration means for insuring reproducible positioning of the tube flange relative to the mounting flange;

(c) adjustment means for moving the X-ray tube in three dimensions by adjusting the position of the tube flange relative to the mounting flange and adjusting the tube relative to the tube flange so as to place the focal spot at the desired position of the intersection of the three beam paths in the calibration instrument; and (d) locking means for fixing the two flanges permanently in relation with one another once the focal spot has been positioned at the intersection of the three beam paths in the calibration instrument.

The preferred calibration instrument further comprises a computer system; a DAS for receiving data from three detectors and providing data to the computer system so that the computer system can store data received from the detectors through the DAS; a suitable power supply for supplying power to the X-ray tube when positioned in the calibration instrument; and a program for determining the displacement needed in three dimensions to move the focal spot of the tube to the desired position where the beam paths of the instrument intersect. The calibration instrument is preferably also used as a testing instrument for measuring X-ray tube parameters that are important to the operation of a CT scanner system and accordingly the calibration instrument includes a program for converting data received from the detectors so that one can determine additional information including:

(a) the focal spot position drift with temperature;

(b) the measured focal spot size in two dimensions;

(c) the fan angle;

(d) the X-ray intensity noise;

(e) the measured motion of the focal spot (wobble and drift) in two dimensions at all relevant frequencies, e.g., from as few as two or three cycles/day to as much as 100 cycles/sec or more;

(f) the measured intensity of the X-rays, for a given voltage and current provided by the power supply; and (g) the measured fluctuations of the X-ray intensity, not due to motion, at all of the relevant frequencies mentioned in (e).

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE DRAWINGS

The invention will be more fully understood from the following detailed description, in conjunction with the accompanying figures, wherein the same or like numerals are used to describe the same or like parts.

DETAILED DESCRIPTION OF THE DRAWINGS

In accordance with one aspect of the present invention, a calibration and testing instrument is provided to align the focal spot of an X-ray tube with a predetermined reference point compatible with desired alignment conditions for using the tube in a CT scanner system.

The alignment is facilitated with an interface registration support for supporting the X-ray tube and is adapted to accommodate relative movement of the X-ray tube that displaces the focal spot relative to the support in any one of three orthogonal directions. Once the proper alignment is determined with the calibration instrument, the as-adjusted X-ray tube and interface registration support are fixed relative to one another so as to form an X-ray tube assembly that is adapted to be mounted to a section of a CT scanner such that the focal spot of the X-ray tube will be automatically aligned with the off-focal aperture, slice-defining aperture and the detector array of the CT scanner system, without the need for subsequent positional adjustment of the tube.

Figure 1:
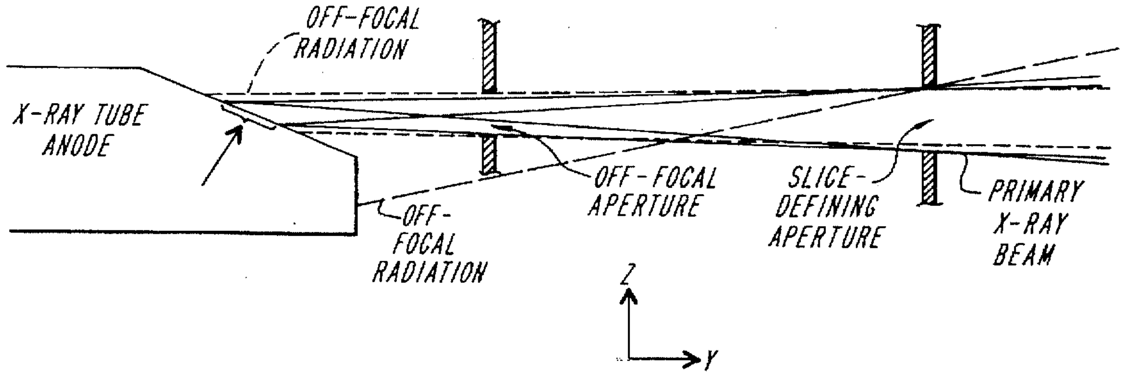
FIG. 1 (PRIOR ART)
FIGS. 1 and 2 are schematic views of the relationship between the focal spot, off-focal aperture, slit-defining aperture and the detector arrays, shown respectively in side view and end view of a typical CT scanner system.
Figure 2:
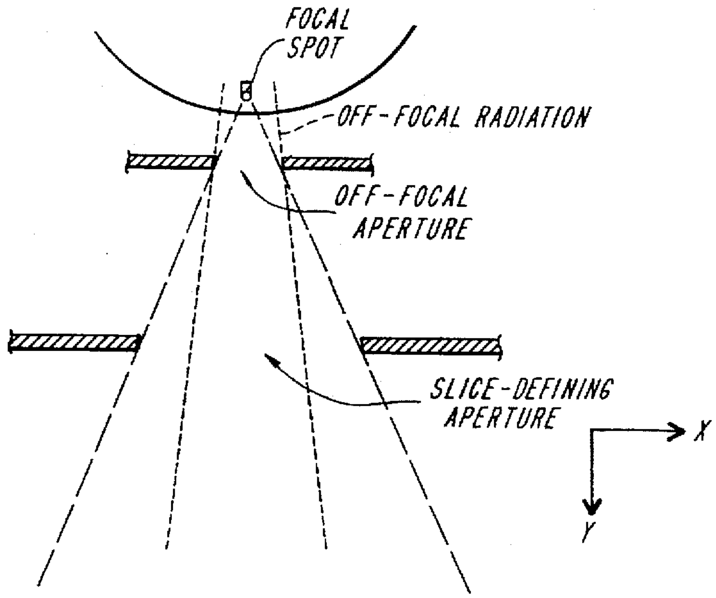
FIG. 2 (PRIOR ART)
Figure 3:
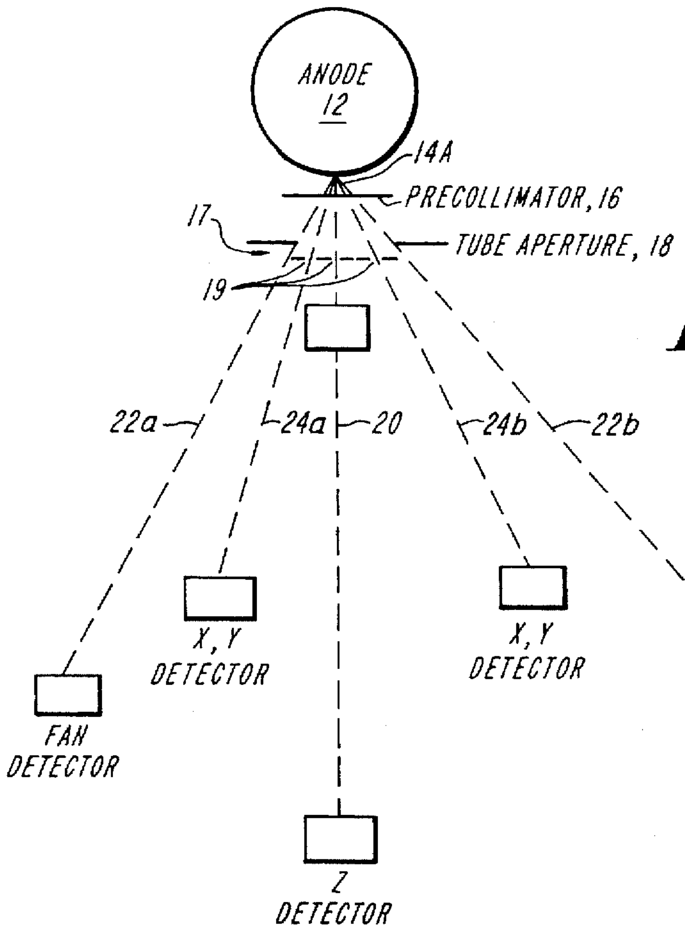
FIG. 3 is a schematic diagram illustrating a frontal view of an X-ray tube calibration and testing instrument designed according to one aspect of the present invention.
Figure 4:
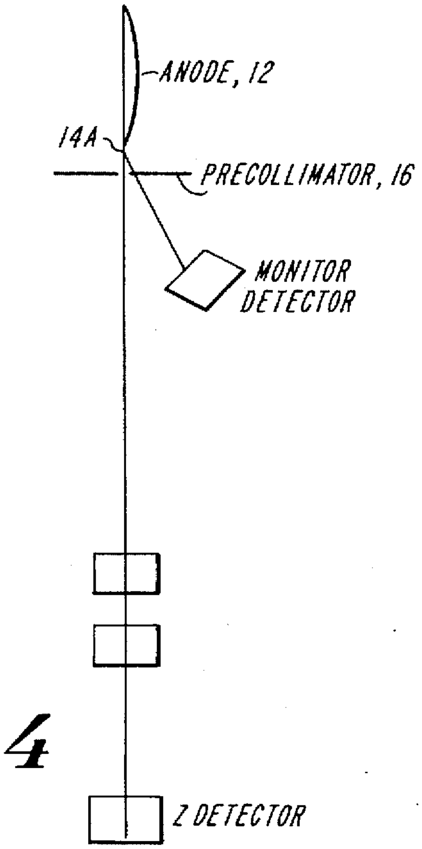
FIG. 4 is a schematic diagram illustrating side view of the X-ray tube calibration and testing instrument shown in FIG. 3.

Referring to FIGS. 3 and 4, schematic diagrams are shown of a preferred calibration and testing instrument 10 for adjusting the position of the focal spot 14 of an X-ray tube assembly including anode 12 defining the focal spot (shown at its correct calibrated position hereinafter referred to as 14A in FIGS. 6 and 8), a precollimator 16, and tube aperture 18. As shown in FIG. 3, the calibration and testing instrument includes means 17 associated with the energy source, such as a system of apertures 19, for defining at least three beam paths 20, 22 and 24 which intersect at the desired position 14A of the focal spot. Each path is provided with at least one detector for detecting the radiation (shown representatively at 20) emitted from the focal spot 14 by anode 12 and received by the respective detector along the beam path, in order to determine the displacement of the focal spot from the desired position 14A. Preferably, a single Z detector is positioned along the beam path 20 which may, for example, pass vertically through the desired position 14A of the focal spot. A pair of fan detectors are positioned along the paths *22a* and *22b*, the paths preferably being positioned on opposite sides of, and may, for example, be symmetrically positioned about the beam path 20. The paths *22a* and *22b* are positioned to detect the edges of the fan beam provided by the focal spot of the tube, the precollimator and tube aperture 18 when the focal spot 14 is at or near the desired position 14A. The fan detectors are provided to detect the fan width of the X-ray emissions as seen in FIG. 3. A pair of X,Y detectors are also positioned on opposite sides of, and may for example, be symmetrically positioned about the beam path 20 within the plane of the fan beam defined by the focal spot 14 at the desired position 14A so as to define the beam paths *24a* and *24b*, so that the Z, fan, and X,Y detectors are all within the same plane as the fan beam when the focal spot 14 is properly positioned at or near the desired position 14A.

As best seen in FIG. 4, a monitor detector is positioned out of the plane of the fan beam for providing a signal for determining the Z axis directed position of the focal spot as well as monitoring the intensity of the X-radiation emanating from the focal spot, as described in greater detail in copending U.S. patent applications: Ser. No. 08/343,240 entitled X-ray Focal Spot Movement Compensation System filed Nov. 22, 1994 in the names of John Dobbs an Ruvin Deych; and Ser. No. 08/343,248 entitled Normalization of Tomographic Image Data filed Nov. 22, 1994 in the names of John Dobbs and Hans Weedon, both assigned to the present assignee, and both incorporated herein by reference.

As is well known, when using a solid state detector, the detector includes a scintillation crystal for converting the high energy X-radiation photons to low energy light photons, and a photodiode for converting the light photons into an electrical signal representative of the number of photons detected. In some instances, the scintillation crystal can be omitted and the photodiode exposed to the radiation. In any event, a particular detector measures the position of the beam to which it is exposed in a direction perpendicular to the long dimension of the scintillation crystals, or the photodiodes. Accordingly, the crystals and photodiodes of the X,Y and fan detectors are oriented perpendicular to the fan beam shown in FIG. 3 (as extending between beam paths 22*a* and 22*b*). The Z detector of FIG. 3, however has its crystals and photodiodes parallel to the fan beam. The precollimator 16 has holes (i.e., apertures) which define the beam position at the surface of each of the detectors shown in FIGS. 3 and 4. Thus, as the focal spot moves, its position is determined in three dimensions by the fan, X,Y and Z detectors designed to measure the X, Y, and Z coordinates of the detected focal spot. Each of the fan, X,Y and Z detectors, as well as the monitor detector, preferably include crystals and photodiodes so as to provide sixteen detection channels. Examples of such detectors are disclosed in copending U.S. patent applications: Ser. No. 08/343,240 entitled X-ray Focal Spot Movement Compensation System filed Nov. 22, 1994 in the names of John Dobbs an Ruvin Deych; and Ser. No. 08/343,248 entitled Normalization of Tomographic Image Data filed Nov. 22, 1994 in the names of John Dobbs and Hans Weedon, both assigned to the present assignee.

Figure 5:
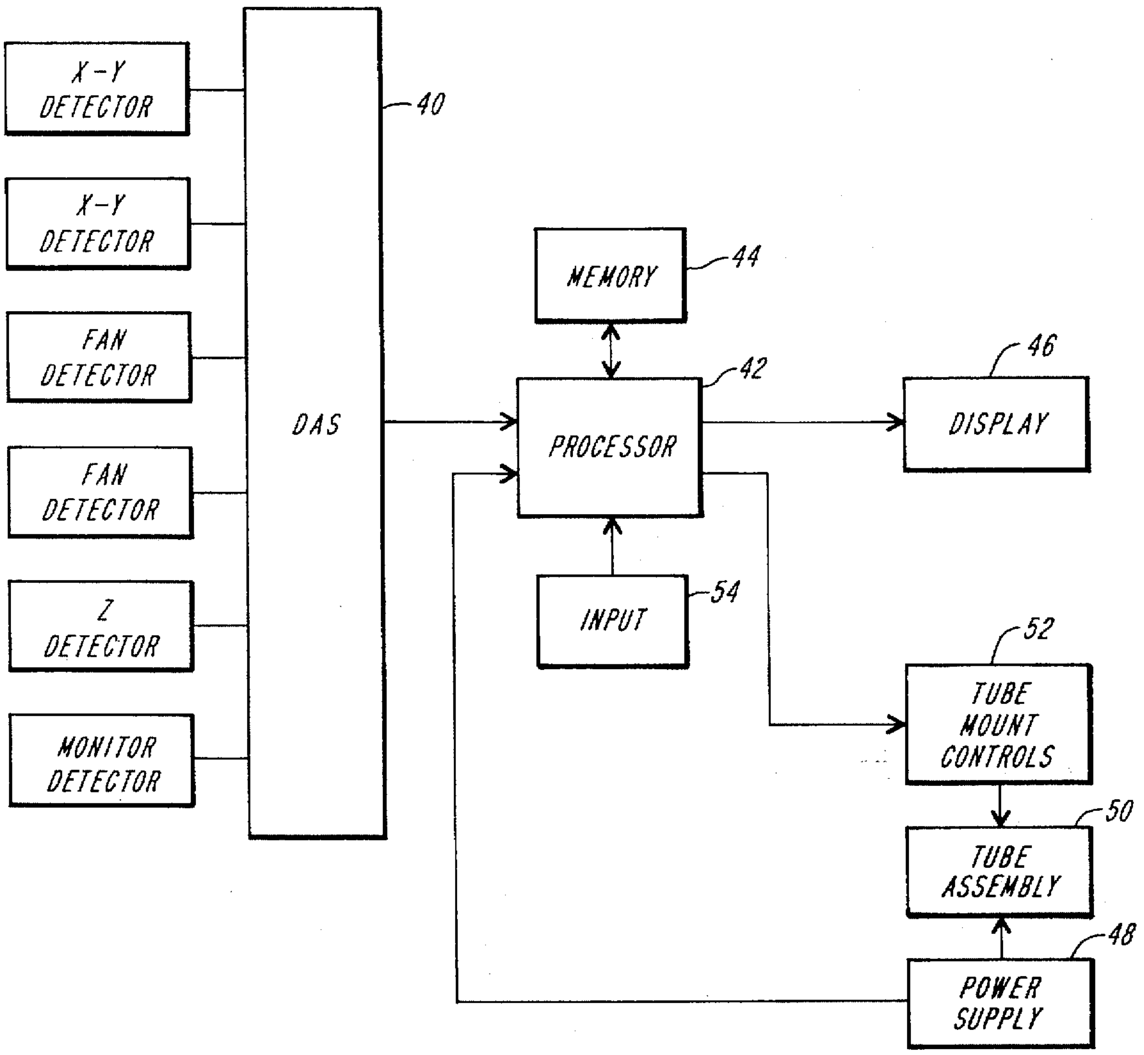
FIG. 5 is a block diagram of the signal process and control system of the calibration and testing instrument shown in FIGS. 3 and 4.

As shown in FIG. 5 the X,Y detectors, fan detectors, Z detector and the monitor detector are connected to a DAS 40, which in turn provides signals as a function of the information provided from the detectors to the processor 42. Memory 44 is provided for storing data, and a display 46 is provided for displaying information to the operator of the calibration testing instrument. A power supply 48 is provided for powering the X-ray tube provided in the X-ray tube assembly indicated at 50 in FIG. 5. Information relating to the current and voltage provided to the X-ray tube assembly 50 is provided to the processor 42. An input 54 is also provided to the processor 42 so that the operator can process the data and make calculations as desired. In one embodiment of the invention, the displacement data is provided on display 46. The operator can then move the tube assembly 50, make the calibrated adjustments, and rerun the calibration test to insure that the focal spot is correctly positioned. In another contemplated embodiment, tube mount controls 52 can be provided for automatically making some or all of the adjustments to the tube assembly based upon the displacement values.

Figure 6:
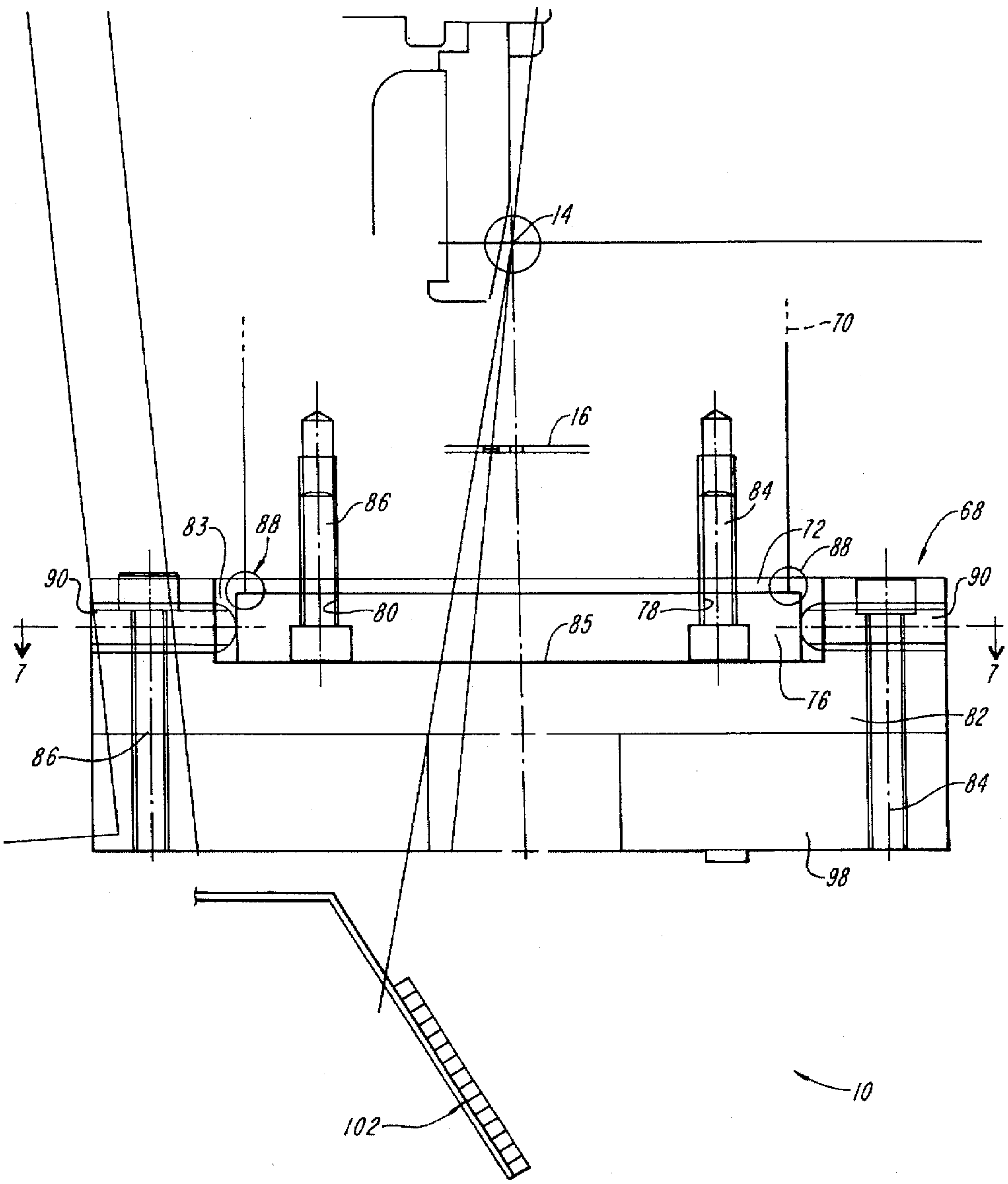
FIG. 6 is a schematic diagram of a preferred embodiment of a test tube assembly positioned within an X-ray tube calibration and testing instrument according to the principles of the present invention.

Referring to FIG. 6, a schematic drawing is shown further detailing mechanical aspects of the calibration and testing instrument 10 of FIGS. 3 and 4 and to illustrate how the X-ray tube (indicated generally at 70) is mounted in the calibration and testing instrument (indicated generally at 10) for adjusting the focal spot 14 so that it coincides with the desired position 14A. In accordance with one aspect of the present invention, the focal spot adjustment is facilitated with an interface registration support 68 that is adapted to receive X-ray tube 70 at its port face coincident with tube aperture plate 72.

Figure 7:
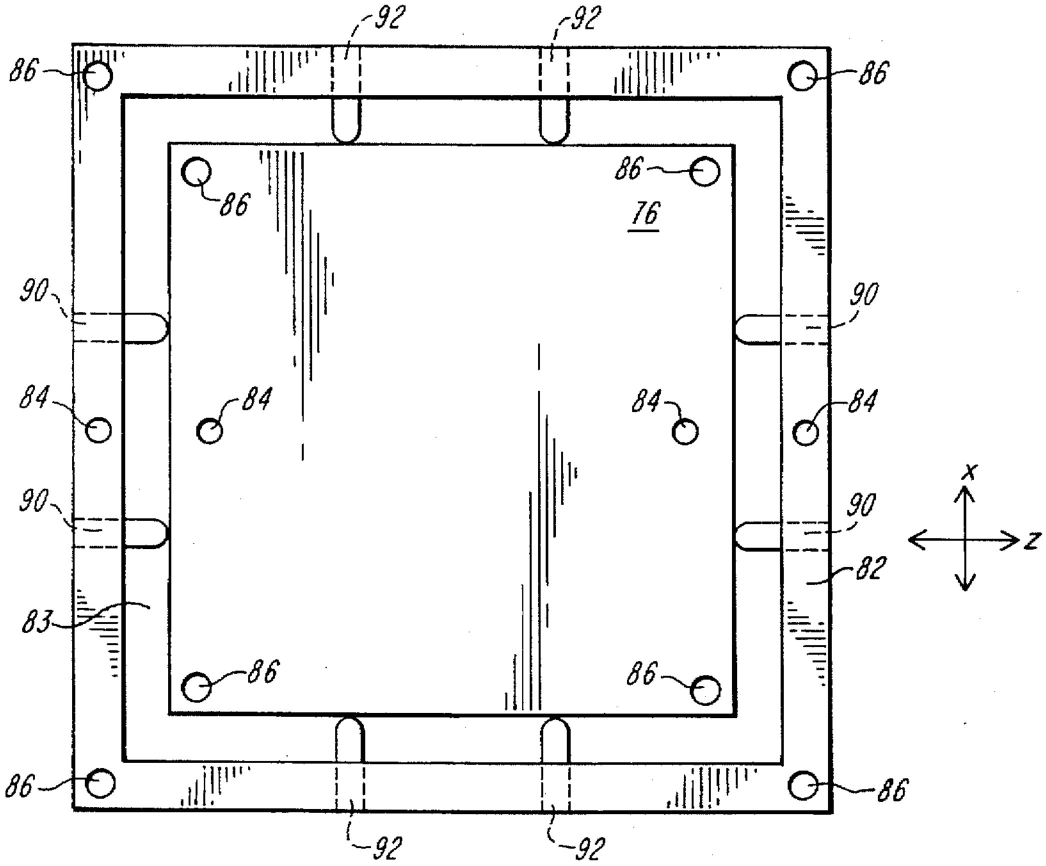
FIG. 7 is a cross sectional view taken along line 7—7 in FIG. 6.

In a preferred embodiment, the interface registration support 68 includes a tube flange 76 fitted with at least two holes 78 and 80 adapted to register with corresponding holes in the base of X-ray tube 70 to securely mount the X-ray tube on an upper face of tube flange 76. Suitable fastening means, such as dowel pins 84 and bolts 86 extending through the holes, are used to register and secure the tube flange and tube together. The dowel pins keep the flange and tube from sliding relative to one another, while the bolts insure that the mutually confronting surfaces remain in contact with one another. Where the adjustments are made automatically with the controls 52 of FIG. 5, the tube and tube flange may be registered together with the dowel pins, without the bolts being attached so as to allow the mutually confronting surfaces of the tube aperture plate and the tube flange to move in the Y direction into and out of contact with one another. Shims can be automatically inserted with controls 52 when necessary based on the displacement measurements in the Y direction. When the adjustments have been completed the bolts can then be used to secure the tube and tube flange together. The interface registration support 68 further includes a mounting flange 82 configured with a mounting plate having a recess 83 for defining a mounting surface 85 for receiving tube flange 76. As best seen in FIG. 7, the length and width of the recess is larger than the length and width of the tube flange 76 so that the tube flange 76 can be moved in the X direction (the direction normal to the plane of FIG. 6 and the vertical direction of FIG. 7) and the Z direction (the horizontal direction in both FIGS. 6 and 7). The movement of the tube flange 76 relative to the mounting flange 82 in the X and Z directions can be effected by set screws 90 and 92 which extend through the sides of the mounting flange into the recess 83. Once adjusted the screws can be tightened. The mounting flange 82 is in turn secured in precise registration with the mounting means of the calibration and testing instrument, i.e., instrument frame 98 with suitable registration means and fastening means, such as a pair of or more dowel pins 108 (one being shown in FIG. 6) and screws 86.

The shim region indicated generally at 88 is adapted to receive shim elements (not shown) for adjusting the vertical positioning of X-ray tube 70 relative to tube flange 76, as measured in the Y direction. The shims preferably are positioned between the tube flange 76 and the tube aperture plate 72 prior to securing the screws 86. Thus, once calibrated the X-ray tube 70, tube flange 76, and mounting flange 82 together form a single assembled unit.

Referring to the operation of the illustrated embodiment, the mounting flange is secured to the instrument frame 98 with screws 86 and dowels 108, and the tube 70 is mounted on a tube flange 76, which in turn is positioned in the recess 83 of the mounting flange. The calibration and testing instrument 10 can then be used to measure the required displacement of the focal spot 14 from the desired position 14A. In addition, various parameters of the tube can be measured. As known to those skilled in the art, X-ray tubes are typically provided from the manufacturer with the focal spot positioned with respect to its port face (i.e., tube aperture 18) with tolerances of ±1 mm in three dimensions. However, this range produces an unacceptable uncertainty in the X-ray emission profile when the X-ray tube is later installed in a CT scanner. It is therefore a primary purpose of calibration and testing instrument 22 to adjust the focal spot position with tolerances preferably on the order of ±0.1 mm. As indicated above, the X-ray tube 70 is mounted on and fastened to tube flange 76. The position of X-ray tube 70 (and hence focal spot 14) is adjusted in the Y direction with the addition or removal of shims in shim region 88, and in the X and Z directions with the appropriate adjustment of set screws 90 and 92 that determine the precise placement of tube flange 76 within the recess 83 of mounting flange 82. The specific adjustments are made by turning the tube 70 on and measuring radiation received by the fan detectors, X,Y detectors, Z detector and monitor detector, and providing the detector outputs to the processor 42 of FIG. 5. The displacement of the focal spot 14 from the desired position 14A is then determined and the adjustments accordingly made. The adjustments can be made by removing the screws 86 so as to remove the assembled unit of the tube 70, tube flange 76 and mounting flange 82 from the instrument frame 98, and making the necessary adjustments independent of the instrument 10. Alternatively, controls 52 can be provided to automatically make one or more of the adjustments without removing the assembly.

In accordance with another aspect of the present invention, the position coordinates of the focal spot 14 are determined using data that reflects the first and second moments of the distribution of energy detected by the detectors shown in FIGS. 3 and 4. The position of the spot on a detector is computed using the first moment or centroid according to the following equation:

$$i_{av}=[\Sigma iQ_i]/[\Sigma Q_i], \tag{1}$$

wherein i is the channel number 1 to 16 and $Q_i$ is the charge coming from the ith detector channel.

In another form of the invention, the focal spot size is identified using a processing facility based on a second moment of distribution of energy. The size of the focal spot is computed using the second moment according to the following equation:

$$s=[\Sigma(i-i_{av})^2Q_i]/\Sigma Q_i. \tag{2}$$

These moment measurements are converted into focal spot position and focal spot size using the geometry of the instrument 10.

Specifically, the entire geometry defining the mounting flange attached to the instrument frame 98 relative to the detectors of instrument 10, is predetermined. Based on the calculated position of the focal spot 14 on the detectors (as determined by the moment measurements), the known geometry of the instrument 10 and the location of focal spot 14 relative to its tube aperture 18, the location of focal spot 14 relative to the detectors can be determined. Once this geometrical relationship is established, adjustments can be made to the focal spot location to achieve a desired alignment condition where focal spot 14 coincides with the desired position 14A. In accordance with the present invention, this alignment condition occurs when the centers of gravity of the detected energy distributions provided by the detector assembly are all symmetric about their respective detection channels. If the energy distribution is viewed as a histogram curve for explanatory purposes, the alignment condition results when the histogram curve for each detector array is symmetrical about its sixteen channels. Since the pitch of the set screws and the thickness of the shim elements is known, for example, the measurements from the calibration and testing instrument 10 are preferably converted into physical distances measured in inches or millimeters that can then be used to formulate the necessary dimensional adjustments, particularly where the adjustments are made after removing the tube assembly from the instrument 10.

The calibration and testing instrument 10 is also useful in determining a variety of operational parameters for X-ray tube 70. These parameters would include focal spot position (in X, Y and Z coordinates) as discussed above; focal spot position drift with temperature; anode wobble in X and Z directions; focal spot size (in X and Z plane); fan angle; X-ray intensity noise; and filament current and voltage as a function of X-ray intensity. Each of these measurements is discussed below.

Concerning the focal spot position, the calibration and testing instrument 10 is used to adjust the focal spot position with respect to the tube flange. The adjustment is made to ±0.075 mm at an average position of the anode. Since the anode typically drifts due to temperature by 0.25 mm in the Z direction, the range of the focal spot position must be measured and the flange adjustment made with the focal spot in the middle of the range. In a preferred calculation, the position is measured both at less than 10% anode heat and more than 85% anode heat. The X-ray tube is adjusted to the average of these two positions. The focal spot motion due to temperature drift in the X and Z directions is the difference between the positions at low and high temperature.

Anode wobble is measured from the time-dependent variation of the detected X-ray distribution. The measurement may be made by plotting the energy profile of a selected channel as a function of time. The resulting data curve will have a strong sinusoidal modulation. The data for all channels is separated into three sets according to the time that the data was obtained: at the peaks of the modulation, at the valleys, and neither at the peak or valley. The X and Z centroids are calculated for the valley and peak data sets. The difference in these centroids is the anode wobble in two dimensions. Generally, if access could be made to a large number of detected radiation samples (≈1000), the X, Y and Z coordinates could be calculated as a function of time, in which the root-mean-square (RMS) of the X,Y,Z coordinate curve would provide a measure of the anode wobble.

The focal spot size, and in particular its width, is computed in X and Z dimensions using the second moment. The second moment has the same calibration as the centroid (first moment) in inches per channel. Concerning the fan angle measurement, the fan angle is defined as the angle at which the intensity has dropped to 50% of its maximum level. The calibration and testing instrument 10 fashions X-ray beams which are defined on their outside edges by the aperture of the tube. The position of the fan edges is then determined by measuring the outside half height points on these outer beams. The X-ray intensity noise is measured by the RMS fluctuation in a detector, and is unaffected by focal spot motion. The middle channels of the monitor detector may be used for this purpose. In order to perform this measurement, it is preferable to have a large amount of raw detector data and additional processing hardware such as an attenuator for the monitor beam or a photodiode monitor detector. The filament current needed to provide a given X-ray intensity should be substantially constant across all X-ray tubes. Otherwise, the power supply should be adjusted when a new tube is used in the calibration and testing instrument 10.

Once precalibrated, the entire assembly of the X-ray tube 70 and the interface registration support 68 (which includes the tube flange 76 and the mounting flange 82) is removed from the calibration and testing instrument 10, representing a single assembled unit. The focal spot adjustments remain intact within the assembled unit due to the fixed positioning of set screws 90 and 92 (which determine the X and Z positions) and the inclusion of any requisite shim elements between the tube flange 76 and tube aperture plate 72 (which determine the Y position). The calibrated position can be insured by using a suitable material, such as a cement, in the recess 83 and around the tube flange to insure the parts remain in place. The assembled unit can be stored until it is necessary to install the unit into a CT scanner system.

Figure 8:
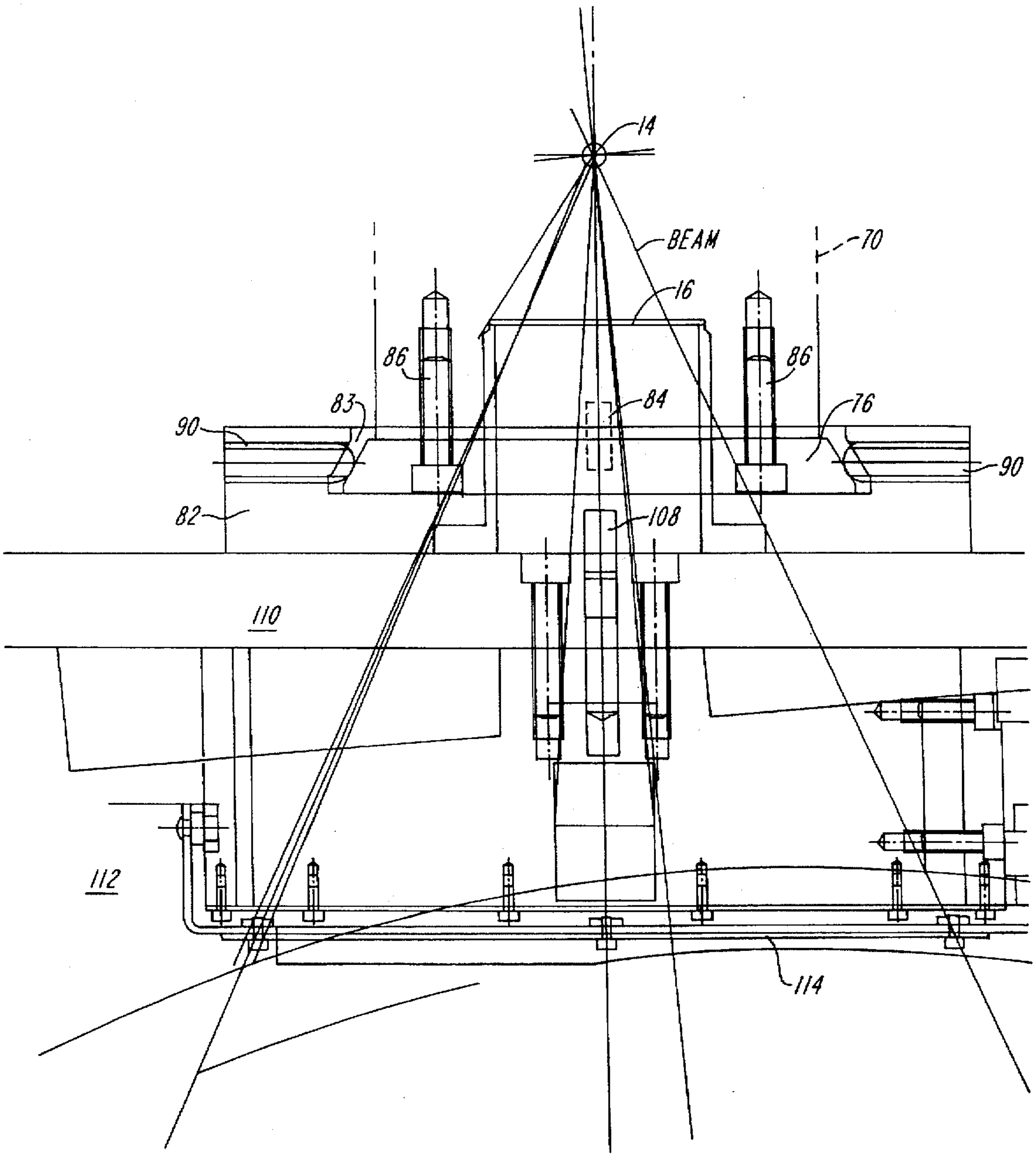
FIG. 8 is a schematic drawing illustrating the installation of the precalibrated X-ray tube assembly in a CT scanner system in accordance with the principles of the present invention.

Referring to FIG. 8, a schematic drawing is shown to illustrate how the X-ray tube 70 which is previously adjusted by calibration and testing instrument 10 is installed in a CT scanner system. FIG. 8 demonstrates only a partial sectional view of a conventional CT scanner system, and in particular shows a portion of a collimator base 110 supported by annular disk 112 (shown in partial section). The assembled unit is installed in the CT scanner by aligning a dowel pin 108 with the mounting flange 82 and within a mating registration channel in the mounting means of the CT scanner system, i.e., collimator base 110 and securing the unit to the base 110 with screws, similar to screws 86. In this regard the instrument frame 98 is constructed identically to the collimator base 110 so that registration of the tube assembly can be easily effected in both systems. Once installed, the integrated unit rests securably on an upper surface of collimator base 110 with the focal spot 14 properly aligned with the off-focal aperture of precollimator 16, the slice-defining aperture of the collimator 114 and detector array (not shown).

The advantage of pre-calibrating the location of the focal spot before installation of the X-ray tube in the CT scanner is that no further alignment procedure is necessary to ensure that the X-ray beam emanating from focal spot 14 will adequately and properly impinge on the scanner detector assembly (not shown) on the disk 112. In fact, typically alignment can be achieved with instrument 10 in about twenty minutes and the tube assembly installed in a CT scanner system in similar amount of time. The geometry of the calibration and testing instrument 10 is specifically chosen in relation to the CT scanner geometry so that when the alignment condition is reached due to the instrument configuration of FIGS. 3,4 and 6, the focal spot 14 will be exactly located at a predetermined desired position 14A required of the scanning operation when the X-ray tube 7.0 is installed in the CT scanner. This known precision of the focal spot and its consequent beam profile within the scanner allows smaller pre-collimating apertures to be used relative to what is required in conventional systems where the location of the focal spot is not as precisely known. This in turn provides better quality images.

While the preferred embodiment has been described in connection with the precalibration of the position of the focal spot of an X-ray tube for use in a CT scanner system, and for testing the operational parameters of the tube, it will be evident to those skilled in the art that the system and method can be used to precalibrate the position of any source of radiation for use in a system where the position of the source is critical to the operation of the system, such as non-medical CT scanner systems as well as other types of scanners such as fourth generation machines, and for testing the source where any one or all of the parameters relating to, for example, beam direction, radiation intensity, stability, etc. is important.

Other modifications and implementations will occur to those skilled in the art without departing from the spirit and the scope of the invention as claimed. Accordingly, the above description is not intended to limit the invention except as indicated in the following claims.

What is claimed is:

1. An apparatus for precalibrating the position of the focal spot of an energy source adapted for use in an energy system prior to mounting the energy source in the energy system so that said focal spot will be correctly positioned within the system when the energy source is mounted in the system, said apparatus comprising:

detector means for receiving and detecting energy emitted by said energy source;

means for defining at least three beam paths which intersect at a predetermined point in space which is the desired spatial position of said focal spot when said energy source is mounted in said energy system;

support means for supporting said energy source; and adjustment means, coupled to said support means, for controllably adjusting the position of said energy source relative to said support means prior to mounting the energy source in the energy system until the detection of energy by said detector means satisfies an alignment condition.

2. The apparatus as recited in claim 1, wherein said energy source is an X-ray tube intended for use in a CT scanner system including a detector array, and said detector means includes at least one detector for detecting the displacement of said focal spot in the Z-axis direction as defined by said scanner system, and said adjustment means moves said tube so that the alignment condition is effective in aligning said energy source with said detector.

3. The apparatus as recited in claim 1, wherein the alignment condition is defined by a geometrical relationship between said focal spot and said detector means that represents a desired alignment of said focal spot with respect to a scan detector array in a computer tomographic (CT) scanner system that is produced if said energy source, as supported by said support means and adjusted by said adjustment means, is integrated with said CT scanner system according to a predetermined mounting scheme.

4. The apparatus as recited in claim 1, further comprising:

analysis means for analyzing the energy detected by said detector means and for determining when said alignment condition is reached.

5. The apparatus as recited in claim 1, wherein said means for defining at least three beam paths comprises a system of apertures associated with said energy source.

6. The apparatus as recited in claim 1, further including means for testing the operational parameters of said energy source.

7. The apparatus as recited in claim 6, wherein the means for testing the operational parameters of said energy source includes means for testing the focal spot position drift with temperature.

8. The apparatus as recited in claim 6, wherein the means for testing the operational parameters of said energy source includes means for measuring the focal spot size in two dimensions.

9. The apparatus as recited in claim 6, wherein the energy source is an X-ray tube, and the means for testing the operational parameters of said energy source include means for measuring the X-ray intensity noise from said tube.

10. The apparatus as recited in claim 6, wherein the means for testing the operational parameters of said energy source includes means for measuring the wobble and drift of the focal spot.

11. The apparatus as recited in claim 6, wherein said energy source is an X-ray tube, said apparatus further includes a power supply for powering said energy source, and wherein the means for testing the operational parameters of said energy source includes means for measuring the intensity of the X-rays emitted by said tube, for a given voltage and current provided by the power supply.

12. The apparatus as recited in claim 6, wherein said energy source is an X-ray tube, said apparatus further includes a power supply for powering said energy source, and wherein the means for testing the operational parameters of said energy source includes means for measuring fluctuations of X-ray intensity of the X-rays emitted by said tube not due to motion of said focal spot.

13. The apparatus as recited in claim 6, wherein the energy source is an X-ray source for use in a fan beam CT scanner system, said X-ray tube includes at least a tube aperture for defining a fan beam angle, and the means for testing the operational parameters of said energy source includes means for measuring the fan beam angle provided from said X-ray source.

14. The apparatus as recited in claim 13, wherein said means for measuring the fan beam angle includes fan beam detector means for detecting the edges of said fan beam.

15. The apparatus as recited in claim 14, wherein said fan beam detector means includes a pair of detectors.

16. The apparatus as recited in claim 1, wherein the energy system comprises (a) system mount means for supporting said support means in a precise position, and (b) at least one other system component positioned so as to be precisely spaced from the desired position of said energy source and said system mount means, said apparatus further comprising:

apparatus mount means for supporting said support means and substantially identical to said system mount means to the extent that when the position of said energy source relative to said support means is at the desired position where the detection of energy by said detector means satisfies the alignment condition, the energy source and said support means can be supported by said system mount means and be correctly positioned in said energy system relative to said system component.

17. The apparatus as recited in claim 16, wherein the support means comprises:

source flange means for securing said energy source to said support means;

mount flange means for securing said support means to either one of said apparatus mount means and system mount means;

adjustment means for adjusting the position of said energy source relative to said mount flange means; and locking means for fixing said source flange means and said mount flange means permanently relative to one another after said focal spot has been positioned at the intersection of said three beam paths.

18. The apparatus as recited in claim 17, wherein said adjustment means includes means for moving said source flange means relative to said mount flange means so as to move said focal spot of said energy source in at least one direction.

19. The apparatus as recited in claim 17, wherein said adjustment means includes means for automatically moving said energy source relative to said source flange.

20. The apparatus as recited in claim 17, wherein said adjustment means includes means for moving said source flange means relative to said mount flange means so as to move said focal spot of said energy source in at least two mutually orthogonal directions.

21. The apparatus as recited in claim 20, wherein said adjustment means includes means for moving said energy source in a third direction normal to said two mutually orthogonal directions.

22. The apparatus as recited in claim 21, wherein said adjustment means includes means for moving said energy source relative to said source flange.

23. The apparatus as recited in claim 16, wherein the energy system is an X-ray imaging system, said system component includes X-ray detection means, and said energy source is an X-ray tube.

24. The apparatus as recited in claim 23, wherein the energy system is a CT scanner system, said system component includes an array of X-ray detectors, and said desired position of said energy source is the position of the focal spot for performing a CT scan.

25. A method of correctly positioning the focal spot of an X-ray source in a CT scanning system of the type including beam defining aperture means and detector means for receiving X-rays from said source passing through said aperture means, said method comprising the steps of:

precalibrating the position of the focal spot position of said X-ray source prior to mounting the source in the scanning system; and positioning the X-ray source in said scanning system without the need to calibrate the position of the focal spot relative to the aperture means and detector means of the CT scanning system.

26. An apparatus for precalibrating the position of the focal spot of an energy source adapted for use in an energy system prior to mounting the energy source in the energy system so that said focal spot will be correctly positioned within the system when the energy source is mounted in the system, said apparatus comprising:

detector means for receiving and detecting energy emitted by said energy source;

means for defining at least three beam paths which intersect at a predetermined point in space which is the desired spatial position of said focal spot when said energy source is mounted in said energy system;

support means for supporting said energy source; and adjustment means, coupled to said support means, for controllably adjusting the position of said energy source relative to said support means prior to mounting the energy source in the energy system until the detection of energy by said detector means satisfies an alignment condition, wherein the energy system comprises (a) system mount means for supporting said support means in a precise position, and (b) at least one other system component positioned so as to be precisely spaced from the desired position of said energy source and said system mount means, said apparatus further comprising:

apparatus mount means for supporting said support means and substantially identical to said system mount means to the extent that when the position of said energy source relative to said support means is at the desired position where the detection of energy by said detector means satisfies the alignment condition, the energy source and said support means can be supported by said system mount means and be correctly positioned in said energy system relative to said system component, wherein the support means comprises:

source flange means for securing said energy source to said support means;

mount flange means for securing said support means to either one of said apparatus mount means and system mount means; and adjustment means for adjusting the position of said energy source relative to said mount flange means, wherein said adjustment means includes means for moving said source flange means relative to said mount flange means so as to move said focal spot of said energy source in at least two mutually orthogonal directions and in a third direction normal to said two mutually orthogonal directions.

27. The apparatus as recited in claim 26 wherein said adjustment means includes means for moving said energy source relative to said source flange.

28. The apparatus as recited in claim 26, wherein said means for defining at least three beam paths comprises a system of apertures associated with said energy source.

29. An X-ray imaging system of the type including X-ray detector means for sensing predetermined radiation, means for supporting an X-ray source relative to said detector means, and aperture means for defining with said X-ray source an X-ray beam directed at said detector means, said system further comprising:

an apparatus for precalibrating the position of the focal spot of said X-ray source prior to mounting the X-ray source in the X-ray imaging system so that said focal spot will be correctly positioned within the system when the X-ray source is mounted in the system, said apparatus comprising:

adjustment means, coupled to said support means, for controllably adjusting the position of said X-ray source relative to said support means prior to mounting the X-ray source in X-ray imaging system until the detection of energy by said detector means satisfies an alignment condition.

30. An apparatus for precalibrating the position of the focal spot of an energy source adapted for use in an energy system prior to mounting the energy source in the energy system so that said focal spot will be correctly positioned within the system when the energy source is mounted in the system, said apparatus comprising:

detector means to receiving and detecting energy emitted by said energy source;

means for defining at least three beam paths which intersect at a predetermined point in space which is the desired spatial position of said focal spot when said energy source is mounted in said energy system;

support means for supporting said energy source; and adjustment means, coupled to said support means, for controllably adjusting the position of said energy source relative to said support means prior to mounting the energy source in the energy system until the detection of energy by said detector means satisfies an alignment condition, wherein said apparatus further includes means for testing the operational parameters of said energy source, wherein the energy source is an X-ray tube, and the means for testing the operational parameters of said energy source includes means for measuring the X-ray intensity noise from said tube.

31. The apparatus as recited in claim 30, wherein said means for defining at least three beam paths comprises a system of apertures associated with said energy source.

* * * * *